United States Patent

Rothe et al.

[11] 4,245,096
[45] Jan. 13, 1981

[54] BIS-(2,4-DINITROPHENYL)-METHYL-PYRIDINIUM AND QUINOLINIUM COMPOUNDS

[75] Inventors: Anselm Rothe, Birkenau; Werner Güthlein, Mannheim; Walter Rittersdorf, Mannheim; Wolfgang Werner, Mannheim, all of Fed. Rep. of Germany

[73] Assignee: Boehringer Mannheim GmbH, Mannheim, Fed. Rep. of Germany

[21] Appl. No.: 34,720

[22] Filed: Apr. 30, 1979

[30] Foreign Application Priority Data

May 17, 1978 [DE] Fed. Rep. of Germany ....... 2821501

[51] Int. Cl.$^3$ .................. C07D 213/26; C07D 215/10; C07D 215/12; C07D 217/10
[52] U.S. Cl. ..................... 546/180; 546/333; 546/149; 422/56
[58] Field of Search .......... 546/333, 149, 180

[56] References Cited

U.S. PATENT DOCUMENTS

| | | | |
|---|---|---|---|
| 2,632,761 | 3/1953 | Cheney | 546/333 |
| 2,764,590 | 9/1956 | Kottler et al. | 546/333 |
| 3,290,281 | 12/1966 | Weinstein et al. | 546/333 |
| 3,627,469 | 12/1971 | Cheng | 546/333 |

FOREIGN PATENT DOCUMENTS 2626367  12/1976  Fed. Rep. of Germany .

Primary Examiner—Henry R. Jiles
Assistant Examiner—Natalia Harkaway

[57] ABSTRACT

Bis-(2,4-dinitrophenyl)-methylpyridinium compounds useful as a pH indicator or for the detection of ammonia having the formula:

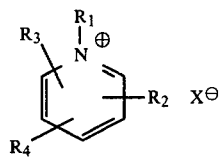

wherein one of
  $R_1$ and $R_2$ is a bis-(2,4-dinitrophenyl)-methyl radical and the other is a lower alkyl radical;
  $R_2$ can also be hydrogen atom or trifluoromethyl;
  $R_3$ and $R_4$ are hydrogen or, together with the carbon atoms to which they are attached, represent a benzene ring; and
  $X^\ominus$ is an appropriate acid anion
or said compounds are betaines.

10 Claims, 2 Drawing Figures

Absorption spectra of Bis-(dinitrophenyl)-4-t.butylpyridino-methanide

| | |
|---|---|
| Concentration | C = 3.58 x 10$^{-5}$ Molar |
| Solvent | Methanol +10% Phospate Buffer pH 10 |
| Pathlength | d = 1.0 cm. |

Absorption spectra of Bis-(dinitro-phenyl)-4-t.butylpyridino-methanide

Concentration    C = 3.58 x 10⁻⁵ Molar
Solvent          Methanol + 10% Phospate Buffer pH 10
Pathlength       d = 1.0 cm.

BIS-(2,4-DINITROPHENYL)-METHYL-PYRIDINIUM AND QUINOLINIUM COMPOUNDS

BACKGROUND

This invention relates to bis-(2,4-dinitrophenyl)-methyl-pyridinium compounds, the preparation thereof and with their use as pH indicators and ammonia detectors.

Remission photometry has established itself in clinical chemistry because of the simple and uncomplicated evaluation of test strips and of the savings in costs thereby achieved.

The measurements are to be carried out with devices which are as economical as possible and which, in contradistinction to spectral and linear photometers, operate in a wide spectral range. A device of this kind is described, for example, in German Pat. No. 2,056,232.

In order to ensure a sufficient sensitivity of measurement, test strips which are to be measured with these devices must contain indicators which do not display steep absorption peaks but rather have broad absorption bands.

A large portion of the absorption bands are to be adapted to the emission characteristic of the fluorescent lamps which are preferably used in such devices and thus lie above 600 nm. Furthermore, it is required of the indicators that the molecular form which is not used for the measurement only absorbs in a range which the remission photometer does not record in order to produce the largest possible color difference and thus to produce a clear measurement signal by the reaction. As a rule, this means that this molecular form must have a colorless to yellow appearance.

A test strip of this kind is, for example, described for the rapid and quantitative determination of glucose in body fluids, such as blood, serum and the like, in German Pat. No. 2,264,438.

In accordance with the above-mentioned requirements demanded of indicators for measurement in inexpensive remission photometers, these test strips contain benzidine derivatives. In their reduced form, these are colorless to yellow and thus absorb in a very low wavelength range. The oxidation products, on the other hand, absorb over a wide wavelength range extending to the region of infra-red.

For the determination of the urea content of blood, hitherto no test strips were known which combined simple handling with short reaction times and a precise remission photometric evaluation. However, especially in cases of emergency, for example in case of uraemic coma, it is essential for the therapeutic measures to be undertaken to have an analytical result which is as accurate as possible in the shortest possible time. However, even in the routine operations of a clinical laboratory, with the introduction of a remissionphotometrically evaluable urea rapid test, a marked advance would be achieved since laborious pipettings, the use of reagents which, in some cases, are of limited stability and corrosive, and long reaction times, would become unnecessary.

The development of such a urea test strip has hitherto not been possible because of the lack of suitable indicators. In contradistinction to the above-described glucose test strips, which use a redox indicator, in clinical chemistry, for the detection of urea, as color indicators in the reaction sequence, use is made of pH indicators for the detection of the ammonia formed.

Two known compounds, hexanitrophenylmethane and ethyl 2-bis-(2,4-dinitrophenyl)-acetate, admittedly possess a usable absorption but, on the other hand, have too low a solubility or too high a pK value.

Other known pH indicators cannot be utilized since either not only the acidic but also the basic form absorb over a broad wavelength range and, therefore, are remissionphotometrically not sharply separated from one another or the colored form only absorbs in a more or less steep peak so that a measurement with simple devices, which only cover a wide wavelength range, is not possible.

SUMMARY

The present invention provides pH indicators which are colorless in their acidic form and strongly colored in their basic form, the coloration being characterized by a broad absorption band. At least one form of these indicators must be sufficiently soluble to enable them to be worked up to give test strips. Furthermore, a sufficiently low pK value, for example of 5 to 10.5, is required to make possible the adjustment of a reasonable pH range for a urea test strip, i.e., permitting the detection of ammonia.

Compounds which fulfill these requirements are bis-(2,4-dinitrophenyl)-methyl-pyridinium compounds of the general formula:

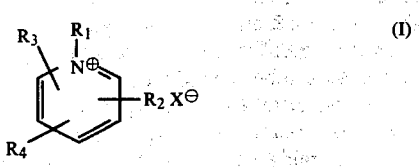

wherein one of the symbols $R_1$ and $R_2$ represents a bis(2,4-dinitrophenyl)-methyl radical and the other a lower alkyl radical, preferably a methyl or tert.-butyl radical, or, in the case of $R_2$ can also represent a hydrogen atom or a trifluoromethyl radical, $R_3$ and $R_4$ represent hydrogen atoms or, together with the carbon atoms to which they are attached, can represent a benzene ring and $X^-$ represents an appropriate acid anion or the compounds are present as betaines.

DESCRIPTION OF THE DRAWING

The present invention will be more fully understood from the following description taken in conjunction with the accompanying drawing wherein.

DESCRIPTION

Figure 1:
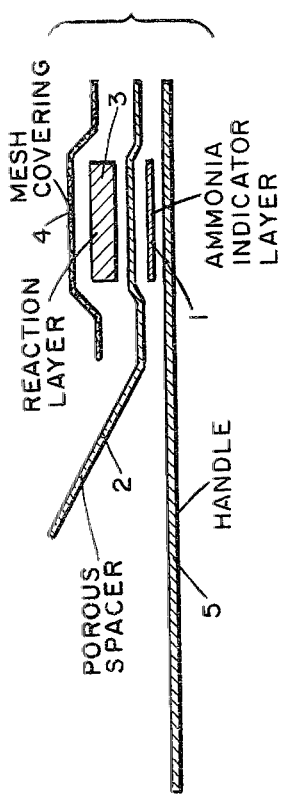
FIG. 1 is an exploded side view of a test device for using a compound of the invention.

The new compounds according to the present invention of general formula (I) can be prepared, for example, by one of the following methods:

(a) nitration of a compound of the general formula:-

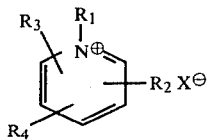

(I')

in which one of the symbols $R_1$ and $R_2$ represents a diphenylmethyl radical and the other symbol has the same meaning as above and $R_{3'}$, $R_4$ and $X^-$ have the same meanings as above; or (b) for the case in which $R_1$ represents a bis-(2,4-dinitrophenyl)-methyl radical, reaction of a compound of the general formula:

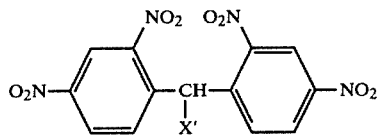

(II)

wherein $X'$ is a chlorine, bromine or iodine atom, with a compound of the general formula:

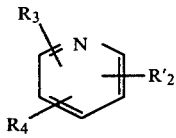

(III), wherein $R'_2$ is a hydrogen atom or a lower alkyl radical and $R_3$ and $R_4$ have the same meanings as above; whereafter, if desired, an $X^-$ group can be replaced in known manner by a different $X^-$ group or, if desired, an alkyl radical $R_1$ can be introduced.

The tetranitration of compounds of general formula (I') requires relatively energetic conditions and is, therefore, preferably carried out with a mixture of fuming nitric acid and oleum at a temperature of from 20° to 100° C., the $X^-$ group thereby being converted into a sulfate group either previously or by means of the excess of sulfuric acid in the reaction medium.

The reaction of the compounds of general formulae (II) and (III) preferably takes place in an excess of compound (III) as solvent, for example, an aromatic hydrocarbon, diethyl ether, dioxan, acetone or the like. The compound (II) can be prepared either from the corresponding, known carbinol by reaction with a hydrohalic acid or from the corresponding methylene compound by reaction with an appropriate halogen in in an inert solvent. These processes can also be employed for the preparation of the starting materials of general formula (I') insofar as these are not known from the literature.

It is especially preferred to dissolve in an excess of the pyridine compound III a methylene compound corresponding to compound (II) and having the general formula:

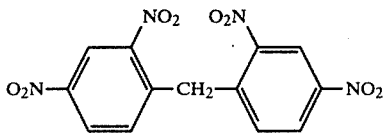

(II')

which can be prepared by nitration of diphenylmethane in the manner described by K. Matsumura (see J.A.C.S., 51, 817/1929), and to produce the compound (II) in situ by the slow addition thereto of a molar amount of bromine or iodine. If desired, an inert solvent, for example, benzene, diethyl ether or the like, can be added thereto. The desired compounds of general formula (II) thereby precipitate out as the sparingly soluble halides.

The introduction of an alkyl radical $R_1$ into the starting compound (I') can be carried out in known manner with an alkylation agent, for example, an alkyl halide, dialkyl sulfate or alkyl-sulfonic acid ester, in an inert solvent, such as toluene, diethyl ether, dioxan, acetone or the like.

The exchange of one $X^-$ group for another one can take place by reaction with an appropriate excess of an appropriate acid HX or preferably of one of its salts, the cation of which forms a sparingly soluble and easily separable salt with the $X^-$ group to be removed. Furthermore, by the addition of a base, for example aqueous ammonia or alkali metal hydroxide, the corresponding betaine compound can be produced which, if desired, can again be converted into a new quaternary salt by the addition of another acid.

The pH indicators according to the present invention are preferably used in urea tests as described in copending application Ser. No. 034,719 filed April 30, 1979. As shown in the following Example 7, the compounds according to the present invention can be used to prepare a quantitative urea test which covers 66.5% of the measurement range of a remission photometer. In the case of the use of a conventional pH indicator, for example, bromophenol blue, only a visually determinable, semi-quantitative test is obtained (see the following Example 8) since it only covers about 23% of the measurement range. Of course, however, the compounds according to the present invention can also be used as pH indicators as such or optionally also together with other pH indicators in mixed indicators for larger pH ranges.

The following examples are given for the purpose of illustrating the present invention:

EXAMPLE 1

1-[Bis-(2,4-dinitrophenyl)-methyl]-4-tert.-butyl-pyridinium halides.

A. Bromide 26.4 g. (0.076 mole) bis-(2,4-dinitrophenyl)-methane are suspended in 125 ml. (114.38 g.; 0.976 mole) tert.-butylpyridine and 12.4 g. (4 ml.; 0.155 mole) dry bromide are slowly added dropwise thereto at 0° to 5° C., while stirring. Thereafter, the reaction mixture is stirred for 6 hours at ambient temperature and the precipitated reaction product is sharply filtered off with suction and washed with 10 ml. tert.butylpyridine. The filter cake is stirred with 100 ml. 10% hydrobromic acid, cooled by placing in an icebath and again sharply filtered off with suction. The filter residue is dissolved, with heating, in 200 ml. methanol, any undissolved material is filtered off with suction and the bromide is precipitated by the addition of 50 ml. diethyl ether. After stirring with 50 ml. acetone, there are obtained 12.42 g. (31.5% of theory) pure 1-[bis-(2,4-dinitrophenyl)-methyl]-4-tert.-butylpyridinium bromide; m.p. 204°–206° C. From the concentrated filtrate and from the worked up mother liquor (acidification with excess 10% hydrobromic acid and suction filtration of the precipitated material), there are obtained, after recrystallization from methanol-diethyl ether and stirring with acetone, a further 4.1 g. (9.3% of theory) of the desired product.

TLC: finished plate, silica gel 60 F 254 (Merck)

Elution agent: isopropanol-ethyl acetate-water (5:3:2 v/v/v);

RF value=0.6 toluene-acetone (3:7 v/v);

RF value=0.6 (both elution agents used in the presence of gaseous ammonia)

Detection: ammonia gas.

B. Iodide

In an analogous manner, there is obtained 1-[bis-(2,4-dinitrophenyl)-methyl]-4-tert.-butylpyridinium iodide; m.p. 217° C.; yield 25.6% of theory (in the preparation, instead of elementary iodine, there is used a solution thereof in tert.-butylpyridine).

C. Chloride

In the same manner, there is also carried out the preparation of 1-[bis-(2,4-dinitrophenyl)-methyl]-4-tert.-butylpyridinium chloride; m.p. 172°-173° C.; yield 31.6% of theory. Instead of elementary chlorine, there is used a solution of chlorine in glacial acetic acid, the process otherwise being as described in A and B above.

Not only the iodide but also the chloride behave in the TLC in the same way as the bromide when using the abovementioned elution agents.

EXAMPLE 2

1-[Bis-(2,4-dinitrophenyl)-methyl]-pyridinium bromide.

The process described in Example 1 is repeated but using pyridine instead of 4-tert.-butylpyridine. There is obtained thin layer-chromatographically uniform 1-[bis-(2,4-dinitrophenyl)-methyl]-pyridinium bromide; M.W. 506.24; m.p. 199°-200° C.; yield 25.6% of theory.

From a methanolic solution of the bromide, there is precipitated out the corresponding tetrafluoroborate by the addition of 35% tetrafluoroboric acid; M.W. 513.26; m.p. 190°-191° C.

TLC: finished plate, silica gel 60 F 254 (Merck) elution agent: acetone; RF value+0.4 detection: UV, ammonia gas.

EXAMPLE 3

1-[Bis-(2,4-dinitrophenyl)-methyl]-quinolinium bromide.

The preparation and working up take place in a manner analogous to that described in Example 1, using quinoline instead of 4-tert.-butylpyridine. By fractional crystallization from methanol-diethyl ether and acetone-diethyl ether, there is obtained chromatographically uniform 1-[bis-(2,4-dinitrophenyl)methyl]-quinolinium bromide; m.p. 186°-188° C.; yield 25.2% of theory.

TLC: finished plate, silica gel 60 F 254 (Merck) elution agent: acetone; RF value+0.6 detection: ammonia gas.

EXAMPLE 4

1-[Bis-(2,4-dinitrophenyl)-methyl]-pyridinium tetrafluoroborate.

16.3 g. (0.05 mole) diphenylmethylpyridinium bromide (obtained from diphenylbromomethane by heating with excess pyridine for 30 seconds at 120° C., evaporating and stirring with diethyl ether; m.p. 216°-219° C.) are dissolved in 30 ml. concentrated sulfuric acid. Carbon dioxide is passed through the solution for 1 hour and the reaction mixture is then heated to 80° C., subsequently cooled to ambient temperature and the sulfuric acid solution added dropwise, within the course of 15 minutes, to a nitration mixture of 30 ml. concentrated sulfuric acid and 8.65 g. fuming nitric acid, the temperature being kept below 50° C. Subsequently, a mixture of 11.4 ml. nitric acid (d.=1.52) and 42.5 g. oleum (15% sulfur trioxide content) is added dropwise thereto, whereafter the reaction mixture is heated to 70° C. for 3 hours and then, after cooling, poured onto 600 ml. ice. The yellow precipitate obtained is dissolved in acetone-isopropanol and again precipitated out by the addition of diethyl ether. The crude product, which, in addition to the desired compound, also contains several by-products, is separated chromatographically on a silica gel column, using acetone as solvent. There are obtained 5.6 g. of the chromatographically uniform, amorphous hydrogen sulfate which is dissolved in methanol and aqueous 38% fluoroboric acid added thereto to give 4.8 g. (20.7% of theory) 1-[bis-(2,4-dinitrophenyl)-methyl]-pyridinium tetrafluoroborate; m.p. 187°-191° C.

EXAMPLE 5

(Diphenylmethyl)-1-methylpyridinium iodides.

0.1 mole of a diphenyl-pyridylmethane is suspended in 200 ml. toluene, 51.25 g. (45 ml.; 0.36 mole) methyl iodide are added thereto and the reaction mixture is heated under reflux for 2 hours. The reaction mixture is then cooled to ambient temperature, 50 ml. diethyl ether are added thereto and the precipitated crystals are filtered off with suction, well washed with diethyl ether and dried over phosphorous pentoxide. Depending upon the substitution of the starting compound, the following products are obtained:

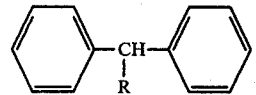

M.W. 387.2

| R | melting point | yield |
|---|---|---|
| 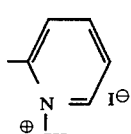 | 228° C. (decomp.) | 98.1% |
| 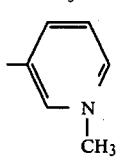 | 160° C. (decomp.) | 91.6% |
| 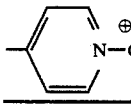 | 152°-155° C. (decomp.) | 96.5% |

(Diphenylmethyl)-1-methylpyridinium nitrates.

0.1 mole of one of the above-mentioned (diphenylmethyl)-1-methylpyridinium iodides is dissolved in 500 ml. methanol, a solution of 0.1 mole silver nitrate in a mixture of 400 ml. methanol and 100 ml. water is added thereto and the reaction mixture is stirred for one hour at ambient temperature, whereafter the silver iodide formed is filtered off with suction and the filtrate evaporated in a rotary evaporator. The distillation residue is dissolved in a little methanol and the nitrate precipitated out by the addition of diethyl ether and drying over phosphorus pentoxide, there is obtained the pure nitrate in the form of colorless crystals, the following compounds being obtained in this manner:

[diphenylmethyl structure, M.W. 322.3]

| R | melting point | yield |
|---|---|---|
| [1-methylpyridinium-4-yl NO₃⁻] | 171° C. | 93.8% |
| [1-methylpyridinium-3-yl NO₃⁻] | 138° C. | 88.4% |
| [1-methylpyridinium-2-yl NO₃⁻] | 176°–178° C. | 96.3% |

[Bis-(2,4-dinitrophenyl)-methyl]-1-methylpyridinium hydrogen sulfates.

17.8 ml. (27.2 g.; 0.431 mole) Nitric acid (d.=1.52) and 90 g. (50 ml.; 0.98 mole) concentrated sulfuric acid (d.=1.84) are placed into a 500 ml. three-necked flask equipped with a stirrer, cooler, thermometer and dropping funnel and, while stirring, 16.1 g. (0.05 mole) of one of the above-mentioned (diphenylmethyl)-1-methyl-pyridinium nitrates are added thereto in such a manner that the temperature of the reaction mixture does not exceed 50° C. Thereafter, the reaction mixture is slowly heated to 70° C. and, at this temperature, a mixture of 60 ml. oleum (15% sulfur trioxide content) and 30 ml. (47.5 g.; 0.75 mole) nitric acid (d.+1.52) is added thereto dropwise and the reaction mixture is heated for 1 hour at 90° C. and subsequently poured onto 500 ml. ice. The crude product obtained is dissolved, with warming, in a little methanol, treated with active charcoal, filtered off with suction and the hydrogen sulfate precipitated out by the addition of diethyl ether. After again dissolving in acetone and precipitating with diethyl ether, there is obtained the chromatographically uniform amorphous hydroxysulfates of the tetranitro compounds, the following compound being obtained in this manner:

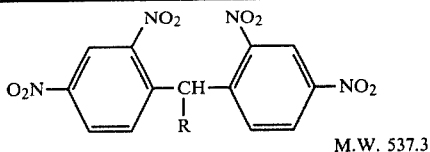

M.W. 537.3

| R | m.p. | yield | TLC* elution agent | RF |
|---|---|---|---|---|
| [1-methylpyridinium-4-yl] HSO₄⁻ | amorphous sinters above 70° C. | 31.5% | XM xylene-methyl ethyl ketone (1:1 v/v) | 0.21 |
| [1-methylpyridinium-3-yl] HSO₄⁻ | amorphous, sinters above 120° C., decomp. | 25.6% | DEW 211 n-butanol glacial acetic acid: water (2:1:1 v/v/v) | 0.19 |
| [1-methylpyridinium-2-yl] HSO₄⁻ | amorphous sinters above 70° C. | 32.1% | isopropanol: n-butyl acetate: water: ammonia (50:30:15:8 v/v/v/v) | 0.45 |

*TLC finished plate; silica gel 60 F 254 (Merck).

Bis-(2,4-dinitrophenyl)-(1-methyl-x-pyridinio)-methanides.

For carrying out the preparation, the above-mentioned hydrogen sulfates are dissolved in water and ammonia or dilute alkali added thereto until the pH is 9–10.5. The deep blue to violet colored pyridiniobetaines formed are filtered off with suction, washed with water and petroleum ether-ligroin (1:1 v/v) and dried over phosphorus pentoxide. These compounds decompose upon heating, without melting. The following compounds are thus obtained:

[structure of bis-(2,4-dinitrophenyl)-(1-methylpyridinio)-methanide, M.W. 438.5]

| position of x | decomposition point | yield | pK value | absorption [nm] |
|---|---|---|---|---|
| 2 | >225° C. | 90.2% | 9 | 400–800 |
| 3 | >238° C. | 93.5% | 10.5 | 400–900 |
| 4 | >233° C. | 95.1% | 6.5 | 400–810 |

EXAMPLE 6

Bis-(2,4-dinitrophenyl)-(4-tert.-butyl-1-pyridinio-methanide.

40 g. (0.071 mole) 1-[bis-(2,4-dinitrophenyl)-methyl]-(4-tert.-butyl-1-pyridinium) bromide or tetrafluoroborate (prepared from a methanolic solution of the crude bromide by the addition of 38% tetrafluoroboric acid; m.p. 204°–205° C.) are dissolved in 200 ml. dimethylformamide with the addition of 2 ml. 485 hydrobromic acid and, with vigorous stirring and monitoring with a glass electrode, the pH is adjusted to 10 by the dropwise addition of 950 ml. 5% ethanolic potassium hydroxide solution.

Thereafter, the precipitated 1-[bis-(2,4-dinitrophenyl)-4-tert.-butyl-1-pyridino]-methanide is poured off, washed with 3 liters of water and the betaine obtained is dried over silica gel and phosphorus pentoxide, there being obtained 33.5 g. (97.8% of theory) of metallically shining crystals of the title compound. The compound decomposes at 225° C., without melting.

TLC: finished plate, silica gel 60 F 254 (Merck)
elution agent: isopropanol:butyl acetate:water (5:3:2 v/v/v/).
RF value = 0.63.

For the preparation of the pyridinium betaine, a dimethylformamide solution of the salt in question can be introduced into a mixture of dimethylformamide and ammonia, the pH is adjusted to 9 to 10, the betaine is subsequently precipitated out by the addition of a fourfold amount of water and the reaction mixture is then further worked up as above.

The following betaines of the following general formula are prepared in the same manner:

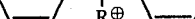

Figure 2:
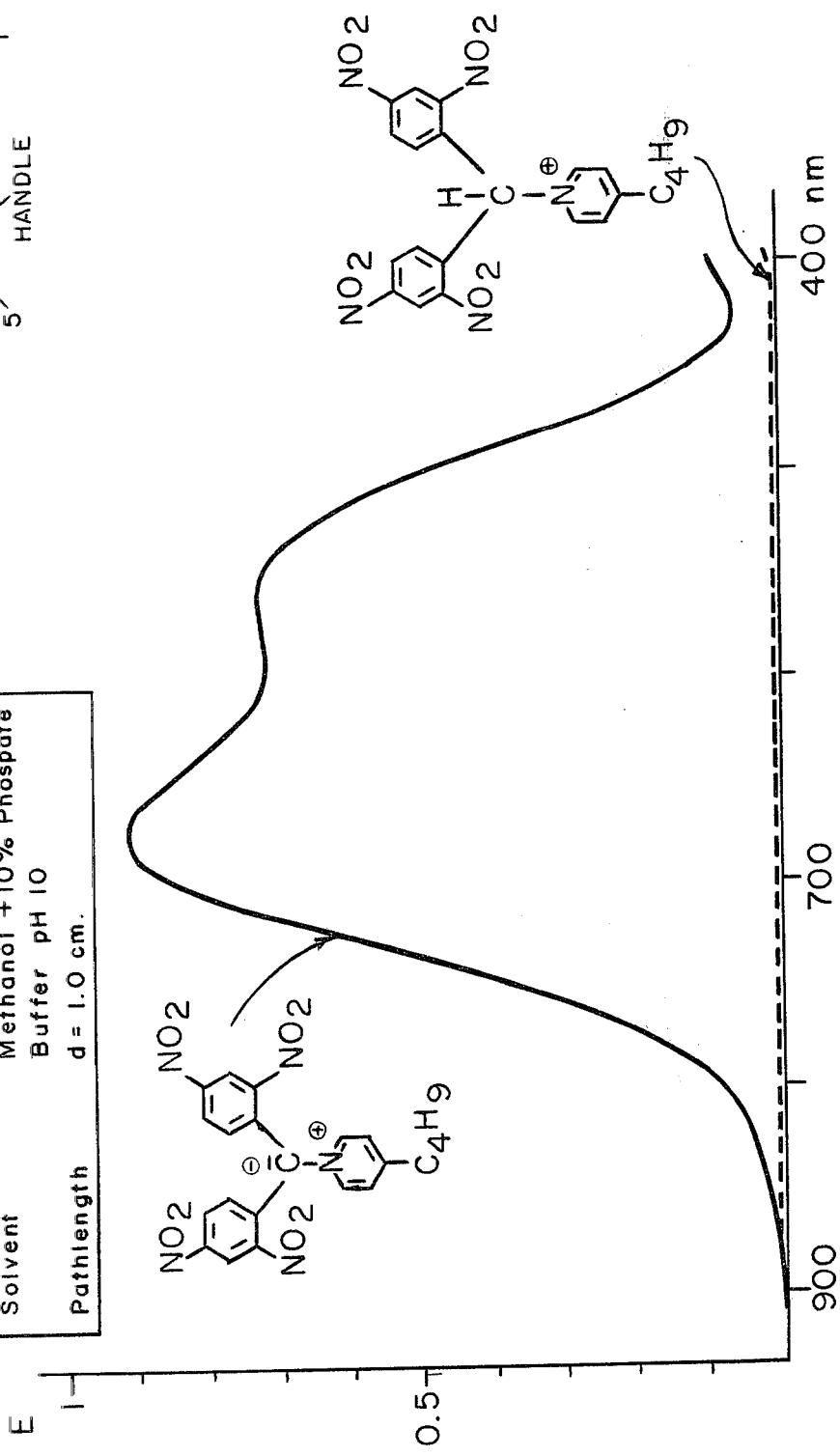
FIG. 2 is a graph plotting the absorption spectra of a compound of the invention.

| $R^\oplus$ | decomposition point | yield | pK-value | absorption (nm) |
|---|---|---|---|---|
| ⊕N—⟨pyridine⟩—C(CH₃)₃ M.W. 481.4 | >225° C. | 97.8% | 8.5 | 400–850 the absorption is shown in Fig. 2 |
| ⊖N—⟨pyridine⟩ M.W. 425.3 | >250° C. | 96.5% | 8.5 | 400–800 |
| ⊕N—⟨quinoline⟩ M.W. 475.3 | >210° C. | 95.6% | 8 | 400–850 |
| ⟨isoquinoline⟩—N⊖ M.W. 475.3 | 230° C. | 96.6% | 7 | 400–850 |

EXAMPLE 7

Quantitative detection of urea in serum (FIG. 1)

A. Urease paper 3

Filter paper is impregnated with a solution of the following composition, dried and cut up into 6 mm. wide bands:

| | |
|---|---|
| urease (5U/mg.) | 6 g. |
| dithioerythritol | 0.1 g. |
| 0.3M TRIS.HCl buffer | 100 ml. (pH 8.5) |

B. Indicator paper 1

Filter paper is impregnated with a solution of the following composition, dried and also cut up into 6 mm. wide bands:

| | |
|---|---|
| N-(bis-(2,4-dinitrophenyl)-methyl)-4-tert.-butyl-pyridinium chloride | 0.39 g. |
| ethylene glycol monomethyl ether | 42 ml. |
| 0.25M sodium malonate buffer (pH 2.8) | 48 ml. |

C. Separator 2

Screen printing cloth with a filament thickness of about 100 μu and an open surface area of about 35%, referred to the total surface area, is hydrophobed with silicone resin and cut up into 25 to 40 mm. wide bands.

D. Covering mesh 4

Hydrophilic nylon mesh of about 60 μu thickness and 40 μu filament thickness and with a free hole surface area of about 65%, referred to the total surface area, is cut up into 15 mm. wide bands.

E. Handle 5

As carrier film and handle, there is used a 6-10 mm. wide approximately 0.2 to 0.3 mm. thick band of melt adhesive-coated polyester film.

Production of the test strips

Urease paper 3, indicator paper 1 and separator 2 are sealed, together with a mesh 4 covering the urease paper on the end of the 6-10 cm. wide handle 5 coated with a melt adhesive and the resulting band cut up into 6 mm. wide strips so that a 6×6 mm. test zone results on a 6-10 cm. long handle.

10 μl. serum are dropped onto the covering mesh of such a strip and closed over with an adhesive label. After a reaction time of 7 minutes, the urease paper and covering mesh are removed, together with the distance piece. The coloration of the indicator layer is measured from above with a remission photometer. Depending upon the urea concentration, the following measurement values are obtained:

| mg. urea/100 ml. serum | measurement signal (scale divisions) ± 1 s, average of 10 values |
|---|---|
| 20 | 12.9 ± 0.75 |
| 40 | 27.5 ± 1.5 |
| 60 | 46.1 ± 1.9 |
| 80 | 61.5 ± 1.4 |
| 100 | 69.0 ± 0.4 |
| 150 | 77.2 ± 0.5 |
| 200 | 79.4 ± 0.5 |

EXAMPLE 8

Semiquantitative detection of urea in blood

A. Urease paper

See Example 7.

B. Indicator paper

Filter paper is impregnated with a solution of the following composition and dried at 70° C.:

| | |
|---|---|
| bromophenol blue | 0.1 g. |
| ethylene glycol monomethyl ether | 9 ml. |
| tartaric acid | 0.4 g. |
| water | 21 ml. |

C. Separator

Polyamide sleece with a thickness of about 80 μu is given a hydrophobic finish with silicone resin.

D. Covering mesh

See Example 7.
Preparation: see Example 7.

For the determination of urea in whole blood, the test strip is provided with a drop of blood. After a reaction time of 7 minutes, visually easily differentiatable reaction colors are formed, depending upon the urea content:

| mg. urea/100 ml. blood | colour |
|---|---|
| 20 | yellow |
| 40 | greenish-yellow |
| 60 | yellow-green |
| 80 | green |
| 100 | blue-green |
| 150 | greenish-blue |
| 200 | blue |

What is claimed is:

1. Bis-(2,4-dinitrophenyl)-methylpyridinium compound of the formula

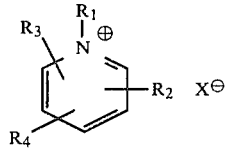

wherein one of
 $R_1$ and $R_2$ is a bis-(2,4-dinitrophenyl)-methyl radical and the other is a lower alkyl radical;
 $R_2$ can also be hydrogen atom or trifluoromethyl;
 $R_3$ and $R_4$ are hydrogen or, together with the carbon atoms to which they are attached, represent a benzene ring; and
 $X^\ominus$ is an appropritate acid anion or the betaine form of said compound.

2. Bis-(2,4-dinitrophenyl)-methylpyridinium compound as claimed claim 1 selected from the group consisting of
1-[Bis-(2,4-dinitrophenyl)-methyl]-4-tert.-butyl-pyridinium bromide;
1-[Bis-(2,4-dinitrophenyl)-methyl]-4-tert.-butyl-pyridinium iodide;
1-[Bis-(2,4-dinitrophenyl)-methyl]-4-tert.-butyl-pyridinium chloride;
1-[Bis-(2,4-dinitrophenyl)-methyl]-pyridinium bromide;
1-[Bis-(2,4-dinitrophenyl)-methyl]-quinolinium bromide;
1-[Bis-(2,4-dinitrophenyl)-methyl[-pyridinium tetrafluoroborate;
Bis-(2,4-dinitrophenyl)-(4-tert.-butyl-1-pyridinio)-methanide;
[Bis-(2,4-dinitrophenyl)-methyl]-1-methyl-2-pyridinium hydrogen sulfate;
[Bis-(2,4-dinitrophenyl)-methyl]-1-methyl-3-pyridinium hydrogen sulfate;
[Bis-(2,4-dinitrophenyl)-methyl]-1-methyl-4-pyridinium hydrogen sulfate;
Bis-(2,4,dinitrophenyl)-(1-methyl-2pyridinio)-methanide;
Bis-(2,4,dinitrophenyl)-(1-methyl-3-pyridinio)-methanide;
Bis-(2,4,dinitrophenyl)-(1-methyl-4-pyridinio)-methanide.

* * * * *

UNITED STATES PATENT AND TRADEMARK OFFICE
CERTIFICATE OF CORRECTION

PATENT NO. : 4,245,096
DATED : January 13, 1981
INVENTOR(S) : Anselm Rothe et al It is certified that error appears in the above-identified patent and that said Letters Patent are hereby corrected as shown below:

Column 1, line 58, delete "remissionphotometrically" and insert -- remission-photometrically --.
Column 2, line 11, delete "remissionphotometrically" and insert -- remission-photometrically --.
Column 3, line 13, delete "(2,4dini-" and insert -- (2,4-dini- --.
Column 6, lines 33 and 34, delete "either" and insert -- ether --.
Column 8, line 7, delete "537.3" and insert -- 537.4 --.
Column 9, line 55, delete "$\oplus_N$" and insert -- $\oplus_N$ --.

Column 10, line 51, delete "u" before "thickness".
Column 10, line 46, delete "u" before "and".
Column 10, line 52, delete "u" before "filament".
Column 11, line 40, delete "u" before "is".
Column 12, line 52, delete "2◯pyridinio" and insert -- 2-pyridinio --.
Column 12, line 27, delete "appropritate" and insert -- appropriate --.

Please add the following claims --
3. Compound as claimed in claim 1 wherein $R_1$ is a bis-(2,4-dinitrophenyl)-methyl radical and $R_2$ is a lower alkyl radical.
4. Compound as claimed in claim 1 wherein $R_1$ is a lower alkyl radical and $R_2$ is a bis-(2,4-dinitrophenyl)-methyl radical at the 2-position.
5. Compound as claimed in claim 1 wherein $R_1$ is a lower alkyl radical and $R_2$ is a bis-(2,4-dinitrophenyl)-methyl radical at the 3-position.

UNITED STATES PATENT AND TRADEMARK OFFICE
CERTIFICATE OF CORRECTION

PATENT NO. : 4,245,096
DATED : January 13, 1981
INVENTOR(S) : Anselm Rothe et al It is certified that error appears in the above—identified patent and that said Letters Patent is hereby corrected as shown below:

6. Compound as claimed in claim 1 wherein $R_1$ is a lower alkyl radical and $R_2$ is a bis-(2,4-dinitrophenyl)-methyl at the 4-position.

7. Compound as claimed in claim 1 wherein $R_2$ is hydrogen.

8. Compound as claimed in claim 1 wherein $R_2$ is trifluoromethyl.

9. Compound as claimed in claim 1 wherein $R_3$ and $R_4$ are hydrogen.

10. Compound as claimed in claim 1 wherein $R_3$ and $R_4$ together with the carbon atoms to which they are attached, represent a benzene ring.

Signed and Sealed this

Eleventh Day of January 1983

[SEAL]

Attest:

Attesting Officer

GERALD J. MOSSINGHOFF
Commissioner of Patents and Trademarks